United States Patent
Blitz et al.

(10) Patent No.: US 8,828,063 B2
(45) Date of Patent: Sep. 9, 2014

(54) FIXATION PLATE FOR USE IN THE LAPIDUS APPROACH

(75) Inventors: Neal Blitz, New York, NY (US);
Michael George, McKinney, TX (US)

(73) Assignee: Amei Technologies, Inc., Wilmington, DE (US)

(*) Notice: Subject to any disclaimer, the term of this patent is extended or adjusted under 35 U.S.C. 154(b) by 663 days.

(21) Appl. No.: 12/274,199

(22) Filed: Nov. 19, 2008

(65) Prior Publication Data
US 2010/0125300 A1     May 20, 2010

(51) Int. Cl.
*A61B 17/04* (2006.01)
*A61B 17/80* (2006.01)

(52) U.S. Cl.
CPC ......... *A61B 17/8061* (2013.01); *A61B 17/8085* (2013.01); *Y10S 606/906* (2013.01)
USPC .......................................... 606/283; 606/906

(58) Field of Classification Search
USPC .................... 606/254, 256, 257, 61, 280–299
See application file for complete search history.

(56) References Cited

U.S. PATENT DOCUMENTS

| | | | |
|---|---|---|---|
| 4,159,716 A | 7/1979 | Borchers | |
| 6,206,882 B1 * | 3/2001 | Cohen | 606/283 |
| 6,344,042 B1 | 2/2002 | Curtis et al. | |
| 7,052,499 B2 | 5/2006 | Steger et al. | |
| 7,344,538 B2 | 3/2008 | Myerson et al. | |
| 2002/0128654 A1 | 9/2002 | Steger | |
| 2005/0065521 A1 | 3/2005 | Steger | |
| 2005/0234458 A1* | 10/2005 | Huebner | 606/69 |
| 2006/0173459 A1 | 8/2006 | Kay | |
| 2006/0241592 A1* | 10/2006 | Myerson et al. | 606/61 |
| 2006/0241607 A1* | 10/2006 | Myerson et al. | 606/69 |
| 2006/0241608 A1* | 10/2006 | Myerson et al. | 606/69 |
| 2007/0239163 A1* | 10/2007 | Strnad et al. | 606/72 |
| 2007/0265629 A1* | 11/2007 | Martin et al. | 606/69 |

FOREIGN PATENT DOCUMENTS

| | | |
|---|---|---|
| FR | 2905590 | 3/2008 |
| JP | 2006-280949 A | 10/2006 |
| JP | 2006-280951 A | 10/2006 |

OTHER PUBLICATIONS

International Search Report of corresponding PCT application No. PCT/US2009/064150.
Supplementary Partial European Search Report of corresponding European Patent Application No. EP09828045.
Morton, D.J., "The Human Foot: Its Evolution, Physiology and Functional Disorders," Columbia University Press, Morningside Heights, N.Y., 1935, Abstract provided.
Japanese Office Action, dated Oct. 1, 2013, JP Application No. 2011-537509, 6 pages.
Communication pursuant to Article 94(3) EPC, EP Application No. 09828045.6, dated Jun. 11, 2013, 5 pages.
Communication pursuant to Article 94(3) EPC, EP Application No. 09828045.6, dated Oct. 5, 2012, 5 pages.
Australian Examination Report, AU Application No. 2009316867, dated Mar. 20, 2014, 3 pages.

* cited by examiner

*Primary Examiner* — Andrew Yang
*Assistant Examiner* — Diana S Jones
(74) *Attorney, Agent, or Firm* — Baker & McKenzie LLP (57) ABSTRACT

The present disclosure generally relates to fixation plates for use in correcting Hallux Valgus deformities under the Lapidus approach. The plate includes holes defined therethrough in such a way to facilitate multiplanar stability across the metatarsocuneiform joint. The plate is further sized and shaped to approximate the natural anatomic contour of the bone segments surrounding the metatarsocuneiform joint. Related methods for using the Lapidus approach to correct Hallux Valgus deformities are also described.

20 Claims, 8 Drawing Sheets

FIXATION PLATE FOR USE IN THE LAPIDUS APPROACH

TECHNICAL FIELD

The present disclosure generally relates to medical devices for use in correcting foot deformities, and methods for surgically installing such devices and correcting such deformities.

BACKGROUND

Figure 1A:
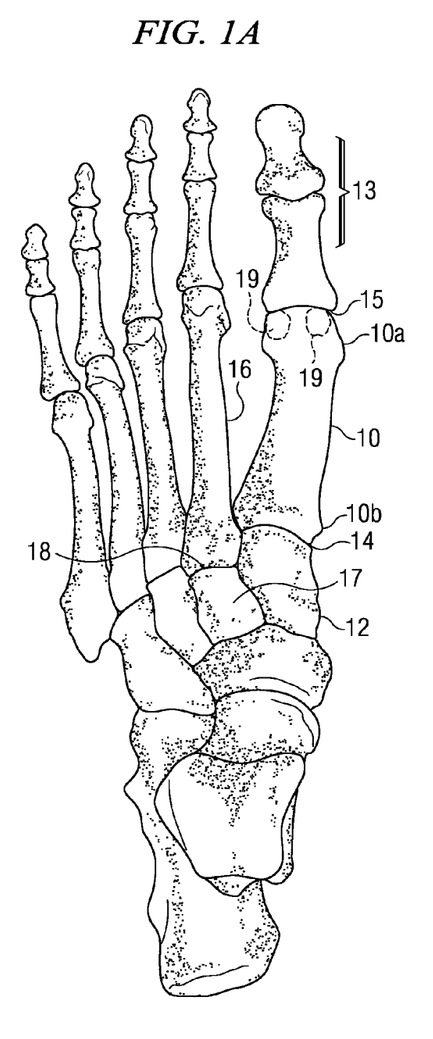
FIG. 1A illustrates a top view of a human foot.

Bunions have long been one of the more common types of painful foot deformities. The technical name for this type of deformity is Hallux Abducto Valgus (HAV), which is generally described as a medial deviation of the first metatarsal accompanied by a lateral deviation and/or valgus rotation of the hallux (or "big toe"). The result effect is a subluxation of the big toe joint (or first metatarsophalangeal joint (MTPJ)) creating a boney prominence (or eminence) on the inside of the foot, near the base of the big toe. FIG. 1A illustrates the normal anatomical configuration of a left human foot, which includes the first metatarsal 10 that extends between the medial cuneiform 12 and the hallux 13. The first metatarsal 10 articulates with the medial cuneiform 12 at the first metatarsocuneiform joint 14 at its most proximal aspect; and is further connected to the hallux 13 at the metatarsophalangeal joint 15 at its most distal aspect. Located adjacent (lateral) to the first metatarsal 10 is the second metatarsal 16, which articulates with the intermediate cuneiform 17 at the second metatarsocuneiform joint 18. The joint between the medial cuneiform 12 and intermediate cuneiform 17 is the intermetatarsocuneiform joint 18. The sesamoids 19 are located beneath (plantar to) the first metatarsal head at the first MTPJ, and articulates with the head of the first metatarsal.

Figure 1B:
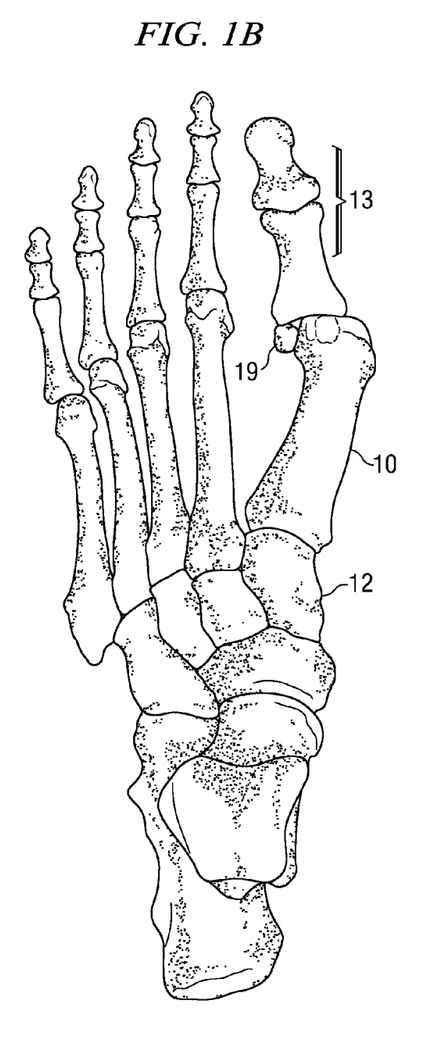
FIG. 1B illustrates a top view of a human foot experiencing the condition of Hallux Valgus.

FIG. 1B illustrates the resulting anatomical configuration of a human foot experiencing HAV. In particular, the first metatarsal 10 extends from the medial cuneiform 12 and deviates medially while the hallux 13 deviates laterally. As a result, the sesamoids 19 may rotate with the first metatarsal 10. This condition may lead to painful motion of the big toe joint and/or difficulty fitting footwear. Other conditions associated with HAV may include: hammer toe formation of the adjacent toes, forefoot pain on the ball of the foot (aka metatarsalgia), stress fractures of the adjacent metatarsals, flat feet (pes planus), and arthritis of the first MTPJ or midfoot.

Bunions may occur from a variety of causes, such as genetic factors, gender influences, biomechanical and structural causes, trauma (injury), and certain shoes. Some physicians believe genetics play a large role in the development of bunions. Dudley Morton suggested that bunions may be a result of evolutionary influence, and described a certain foot type that is associated with bunions—the so called Morton's foot (a condition where the first metatarsal is shorter than the other metatarsals. See Morton DJ. The Human Foot: Its evolution, Physiology and functional Disorders. Columbia University Press, Morningside Heights, N.Y., 1935. Some people develop bunions when associated with a condition called hypermobility, where the midfoot (i.e., metatarsocuneiform joint or "MCJ," illustrated in FIG. 1A as the joint defined at the meeting of the metatarsal 10 and the cuneiform 12) exhibits excessive motion. Less commonly, malshaped bones (hallux and/or first metatarsal) may give the appearance of and/or cause bunions. Many physicians attribute the progressive development of bunions to high heel and pointy toe shoes more commonly worn by women. It is well known that women are more likely to develop bunions than men.

Surgeons use weightbearing radiographs to determine the severity of HAV in an attempt to quantify the deformity, and aid in surgical decision making. The most commonly utilized radiographic measurement is the intermetatarsal angle (IMA), which measures the angle between a longitudinal bisection of the first and second metatarsal shafts. The IMA essentially measures the extent with which the first metatarsal has deviated (medially) from the second metatarsal. The normal value for the IMA is less than 8 degrees. Another useful radiographic measurement is the hallux abductus angle (HAA), which measures the amount of lateral deviation of the big toe (hallux). The HAA essentially measures the extent with which the hallux has deviated (laterally) from its native position (nearly rectus with the more proximal metatarsal). The normal value for the HAA is less than 12 degrees. A patient with a mild HAV deformity may have an IMA of 10-12 degrees and an HAA of 21-30 degrees. A patient with a moderate HAV deformity may have an IMA of 12-16 degrees and an HAA of 31-40 degrees. A patient with a severe HAV deformity may have an IMA of greater than 16 degrees and an HAA of greater than 40 degrees.

Various techniques have been developed to surgically correct HAV. The most basic technique simply involves resecting any enlarged bone at the medial aspect of the first metatarsal head, but this approach is typically used in conjunction with other more advanced techniques. A common technique involves an osteotomy (bone cut) procedure in which the first metatarsal is broken into two pieces and the distal portion of the bone is translated closer (medially) to the adjacent second metatarsal. The osteotomy may be performed at several locations on the first metatarsal, depending on the severity of the deformity. Less severe HAV deformities are typically corrected with an osteotomy near the head (10a in FIG. 1) of the first metatarsal, whereas moderate and larger deformities are corrected with an osteotomy near the base (10b in FIG. 1) of the first metatarsal. Whichever osteotomy technique is utilized, only the distal portion of the first metatarsal is relocated into a more lateral position while the proximal segment position remains unchanged. It should be understood that any osteotomy procedure reorients the first metatarsal by changing its shape from that of a straight bone to a more curved bone.

Alternative techniques have been developed that do not require breaking of the bone, or changing the natural shape of the first metatarsal. One such technique calls for fusion of the MCJ, wherein the entire first metatarsal is relocated into a corrected position. This approach was originally developed by Dr. Paul Lapidus, and hence this particular technique is often referred to as the Lapidus approach (or Lapidus Bunionectomy or Lapidus Arthrodesis or Modified Lapidus Bunionectomy/Arthrodesis). In some situations the procedure may involve an isolated fusion of the $1^{st}$ MCJ, and in other situations surgeons may also incorporate a fusion of the intermediate cuneiform area and or $2^{nd}$ metatarsal base. In general, the idea behind the Lapidus approach is to permanently fuse the base of the first metatarsal to the medial cuneiform bone in a corrected new position. This permanent fixation is carried out by first reducing the IMA and then fusing the MCJ. Implementation of this approach often involves the use of a number of screws across the joint or a plate that can accommodate screws to attach the plate to the metatarsal and medial cuneiform. In some cases, a fusion of the $1^{st}$ MCJ that incorporates lengthening of the entire segment by adding bone graft (i.e., a block of bone) into the fusion site is better termed a distraction Lapidus.

BRIEF SUMMARY

The present disclosure generally relates to an improved fixation or "Lapidus" plate for use in treating HAV deformities or other conditions that may call for a fusion of this joint and possibly concomitant fusion incorporating the $2^{nd}$ metatarsal base and/or intermediate cuneiform. The term "Lapidus" as used herein is only meant to be descriptive in terms of a suggested use for the plate and does not confer any structural limitations on the plate described herein. In one exemplary embodiment, the Lapidus plate is used for joint arthrodesis at the first MCJ. The Lapidus plate according to the present disclosure provides mechanical stability of the first metatarsal while also accommodating and assisting reorientation of the first metatarsal to correct the HAV deformity. In one embodiment, the plate is generally elongated and comprises a thin and rigid stabilizing member of biocompatible material. The orientation of the fixation plate offers multiplanar stability including the plantar aspects of the joint to resist tensile forces transmitted across the fusion site. The screw configuration of the plate can be maintained for several different sizes of the plate while still maintaining desired multiplanar stability. Also, the positioning of the screw holes are designed to avoid invasion of the fusion site by the screws that ultimately pass therethrough. Indeed, the screw angles are designed for the post-Lapidus position.

The Lapidus plate according to the present disclosure includes additional features that accommodate the desired reorientation of the first metatarsal during correction. For example, the Lapidus plate described herein includes a degree of twist along its longitudinal axis to follow the contour of the first metatarsal and medial cuneiform, thereby facilitating reorientation of the first metatarsal to its natural position. The Lapidus plate is further anatomically configured to include a recess, which accommodates the natural crests of the medial cuneiform and the first metatarsal. In this manner, the first metatarsal can be guided against the medial cuneiform and the plate such that the base of the first metatarsal fits within the recess. The recess thus facilitates a desired location and orientation of the first metatarsal that approximates its natural position. In this manner, the Lapidus plate according to the present disclosure accommodates the final position of the fusion of the MCJ. The fixation plate is anatomically configured to provide rigid support of the realigned MCJ fusion site while positioning screws to avoid invasion into the fusion site thus achieving desired stability. It is to be appreciated that the plate described herein can be adapted for use on both right and left feet with a right foot plate being a mirror-image of a left foot plate.

A surgical method for preparing the MCJ for receipt of the Lapidus plate and subsequently implanting the plate is further described. In patients with HAV, surgical procedures may be concomitantly performed near the first metatarsal head. A capsular release of the first MTPJ and resection of the medial eminence, if present, is often performed in conjunction with release of the adductor tendon and lateral sesamoidal ligament. Next, all cartilage is removed from the first MCJ with either a reciprocal saw and/or manual resection. Removal of the cartilage is preferred to allow for bone on bone contact to allow for a fusion between the medial cuneiform and first metatarsal. The first metatarsal is then repositioned back to its native position (IMA as close to zero as possible). However, in order to compensate for the shortening that occurs with removal of the cartilage of the first MCJ, the first metatarsal must be translated inferiorly and/or angulated inferiorly (plantarflexed) to restore the weightbearing mechanics of the first metatarsal head at the ball of the foot. Lastly, the fusion site is stabilized with the fixation plate described herein. In some embodiments, the plate is placed on the dorsal medial surface of the segment to avoid contact with muscular attachments.

BRIEF DESCRIPTION OF THE DRAWINGS

Reference is now made to the following descriptions taken in conjunction with the accompanying drawings.

DETAILED DESCRIPTION

Various aspects of a Lapidus plate and methods of using same according to the present disclosure are described. It is to be understood, however, that the following explanation is merely exemplary in describing the devices and methods of the present disclosure. Accordingly, several modifications, changes and substitutions are contemplated.

Figure 2:
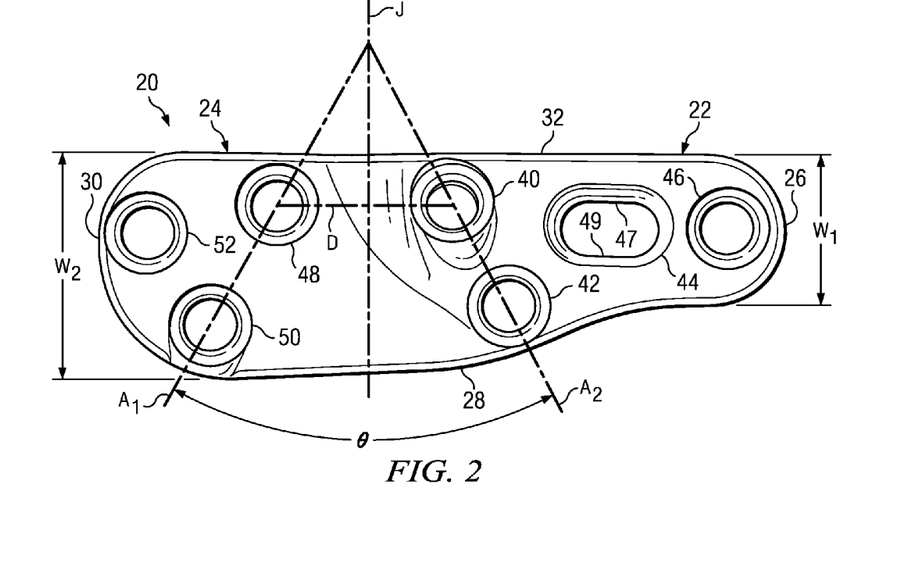
FIG. 2 illustrates a top view of a fixation plate according to one embodiment of the present disclosure.

A Lapidus plate 20 for a human left foot according to the present disclosure is illustrated in FIG. 2. It is to be appreciated that a Lapidus plate according to the present disclosure for a human right foot would be substantially similar to and have a mirror image configuration of the plate 20 illustrated in FIG. 2. The plate 20 generally comprises a distal portion 22 for attachment to a metatarsal and a proximal portion 24 for attachment to a cuneiform. For purposes of illustration only, the distal and proximal portions 22, 24 are divided along a joint axis (J) generally corresponding to the fusion site (i.e., the interface between the cuneiform and metatarsal) as will be described. In one exemplary embodiment, the metatarsal is the first metatarsal 10 (FIG. 1) and the cuneiform is the medial cuneiform (FIG. 1). The plate 20 is sized and shaped to conform to the anatomical contours of the first MCJ and as such the distal portion 22 includes a relatively narrow and rounded end portion 26. The distal portion gradually increases in width along a first side 28 of the plate towards the proximal portion 24. The proximal portion 24 includes a slight gradual increase in width along the first side 28 of the plate 20 culminating in a rounded end portion 30 that is larger in width than the end portion 26 of the proximal portion 22. The plate 20 further includes a substantially linear second side 32 opposite the first side 28.

The plate is configured and designed to avoid tendon and minimize soft tissue irritation, while also providing for optimal rigidity and stability. As such, in some embodiments, the end portion 26 of the distal portion 22 has an anatomically optimal width $W_1$ in the range of 10.5+/−3 mm, while the end portion 30 of the proximal portion 24 has an anatomically optimal width $W_2$ in the range of 16+/−4 mm. In some embodiments, the plate has a varying thickness of between 0.75 mm and 3.0 mm, thus minimizing tissue irritation. Moreover, the edges of the plate may be tapered. In one embodiment, the Lapidus plate according to the present disclosure is sized and shaped for placement in a "safe zone" of the area to be treated; that is, the place on the dorsal medial surface of the first metatarsal and medial cuneiform that is devoid of tendon attachments. It is to be appreciated that the Lapidus plate according to the present disclosure may have a configuration different than that described herein so long as the plate accommodates the contours of the particular anatomical region being treated.

The distal and proximal portions 22, 24 of the plate 20 each include a plurality of screw holes formed therethrough to facilitate attachment of the plate to the respective metatarsal and cuneiform. In one embodiment, the distal portion 22 includes four screw holes formed through the plate 20 with two holes 40, 42 being positioned in proximity to the joint axis J and the remaining two holes 44, 46 being positioned distal of holes 40, 42. In some embodiments, the holes 40, 42 and 46 are countersunk and threaded to accommodate screws having threaded heads as will be described. Hole 40 is positioned adjacent to the second side 32 and the joint axis J while hole 42 is positioned distal of hole 40 and closer to side 28 of the plate 20. Hole 44 is positioned distally of holes 40, 42 and is generally elongated to accommodate movement of the plate 20 as will be described. The elongated nature of hole 44 defines a pair of substantially parallel sides 47, 49, which are substantially parallel to second side 32 of the plate 20. Hole 46 is positioned distal of hole 44 and also accommodates a screw (not shown) to assist with fixation of the plate 20 to the metatarsal. The location of hole 46 assists with distributing weight away from the fusion site.

Similar to the distal portion 22 of the plate 20, the proximal portion 24 includes a plurality of screw holes to accommodate fixation. In one embodiment, the proximal portion 24 of the plate 20 includes three holes 48, 50 and 52 formed therethrough. In some embodiments, the holes 48, 50 and 52 are countersunk and threaded to accommodate screws having threaded heads as will be described. Hole 48 generally corresponds to hole 40 of the metatarsal portion, and as such, is positioned adjacent to the second side 32 and the joint axis J. Hole 50 generally corresponds to hole 42 of the metatarsal portion, and as such, is positioned proximal of hole 48 and closer to side 28 of the plate 20. Hole 52 is positioned proximal of holes 48, 50 and accommodates a screw (not shown) to assist with fixation of the plate 20 to the cuneiform bone. The location of hole 52 assists with distributing weight away from the fusion site.

In one embodiment, the holes 40, 42 of the distal portion 22 and the holes 48, 50 of the proximal portion are designed to assist with screw fixation into the widest part of both bone segments while maintaining a safe distance from the fusion site such that the screws that ultimately pass through such holes do not penetrate the fusion site. In this regard, the holes 40, 42, 48 and 50 form a substantially trapezoidal shape, which facilitates the even distribution of load across the MCJ. It is to be appreciated that the arrangement of holes 40, 42, 48 and 50 may not form an exact trapezoid. For example, the line defined from the centerpoint of hole 40 to the centerpoint of hole 48 and the line defined from the centerpoint of hole 42 to the centerpoint of hole 50 may not be perfectly parallel. Rather, such lines may be only substantially parallel and thus the arrangement of holes 40, 42, 48 and 50 may form a substantially trapezoidal shape rather than a true trapezoidal shape. The substantially trapezoidal arrangement of the holes 40, 42, 48 and 50 define an angle $\theta$ measured between the non-parallel sides of the trapezoid (i.e., between the lines $A_1$ and $A_2$ shown for purposes of illustration in FIG. 2). Also, the distance between the dorsal screw holes 40, 48 is measured by the distance D. In some embodiments, the angle $\theta$ is optimally 57+/−15 degrees and the distance between the dorsal screws 40, 48 is optimally 12+/−4 mm.

Figure 3A:
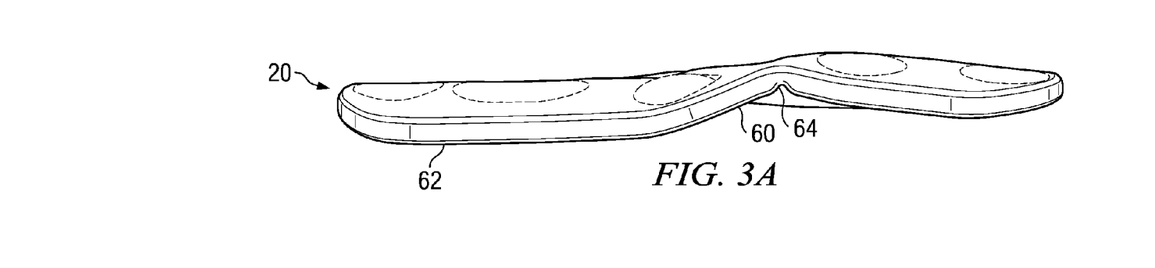
FIG. 3A illustrates a side view of the fixation plate of FIG. 2.
Figure 3B:
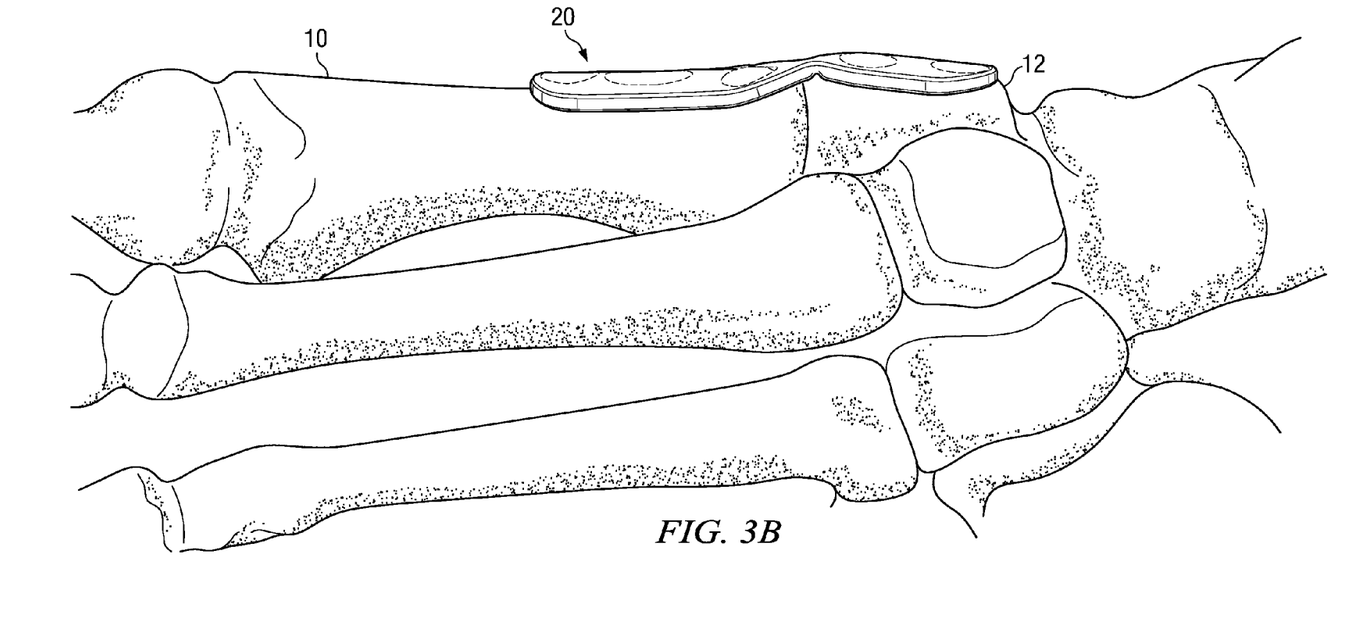
FIG. 3B illustrates a side view of the fixation plate of FIG. 2 positioned adjacent to the MCJ.

Referring to FIGS. 3A and 3B, the plate 20 according to the present disclosure further includes a recess 60 defined along a bone-contacting surface 62 of the plate. The recess 60 is generally defined at and adjacent to the joint axis J of the plate 20. In this manner, the plate 20 is designed to accommodate the crests of the first metatarsal 10 and medial cuneiform 12 upon placement of the plate against the MCJ as illustrated in FIG. 3B. In some embodiments, a channel 64 is formed laterally in the bone-contacting side of the plate 20 in a region generally corresponding to the recess 60 to facilitate additional flexibility at the fusion site along the joint axis J (FIG. 2). This flexibility assists the surgeon with bending of the plate 20 to achieve the desired final position of the plate at the fusion site.

Figure 4:
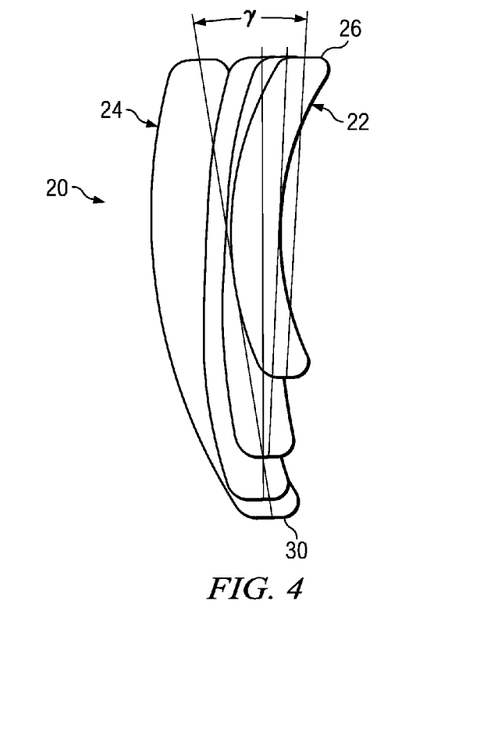
FIG. 4 illustrates a schematic view depicting the gradual twist of the fixation plate of FIG. 2.

In some HAV deformities, the first metatarsal experiences a lateral twist. As a result, the sesamoid bones are no longer in contact with the surface and are thus not able to carry most of the body load transferred through the forefoot during motion. This results in an extra load being placed on other adjacent metatarsals, thus increasing the possibility for metatarsalgia, or possibly stress fractures in those metatarsals. To correct this disorientation, in some embodiments, the plate 20 according to the present disclosure includes a degree of twist along its longitudinal axis (i.e., from end portion 30 to end portion 26 as shown in FIG. 2). Referring to FIG. 4, the plate 20 has a gradual twist $\gamma$ from proximal portion 24 to distal portion 22. In some embodiments, the anatomically optimal twist is 12+/−6 degrees measured along the longitudinal axis of the plate 20 defined from end portion 30 to end portion 26.

Figure 5A:
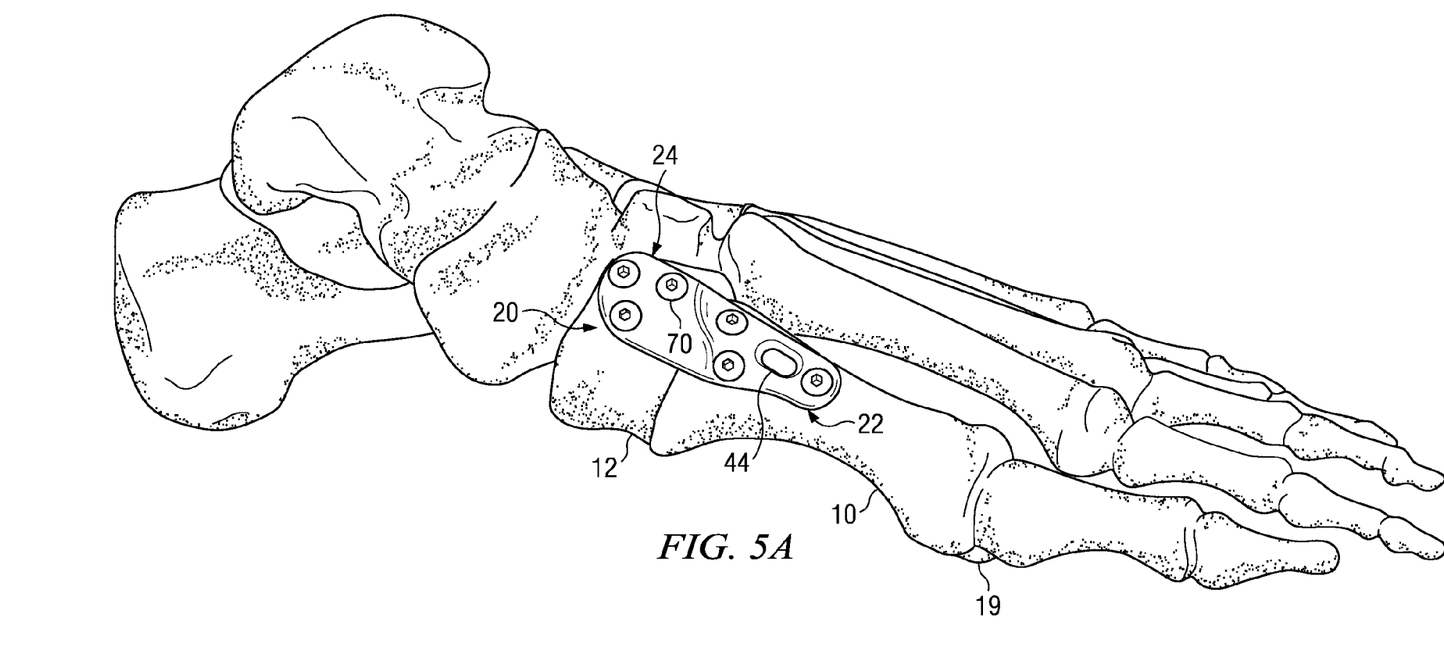
FIG. 5A illustrates a perspective view of the fixation plate of FIG. 2 positioned against the medial cuneiform and first metatarsal.
Figure 5B:
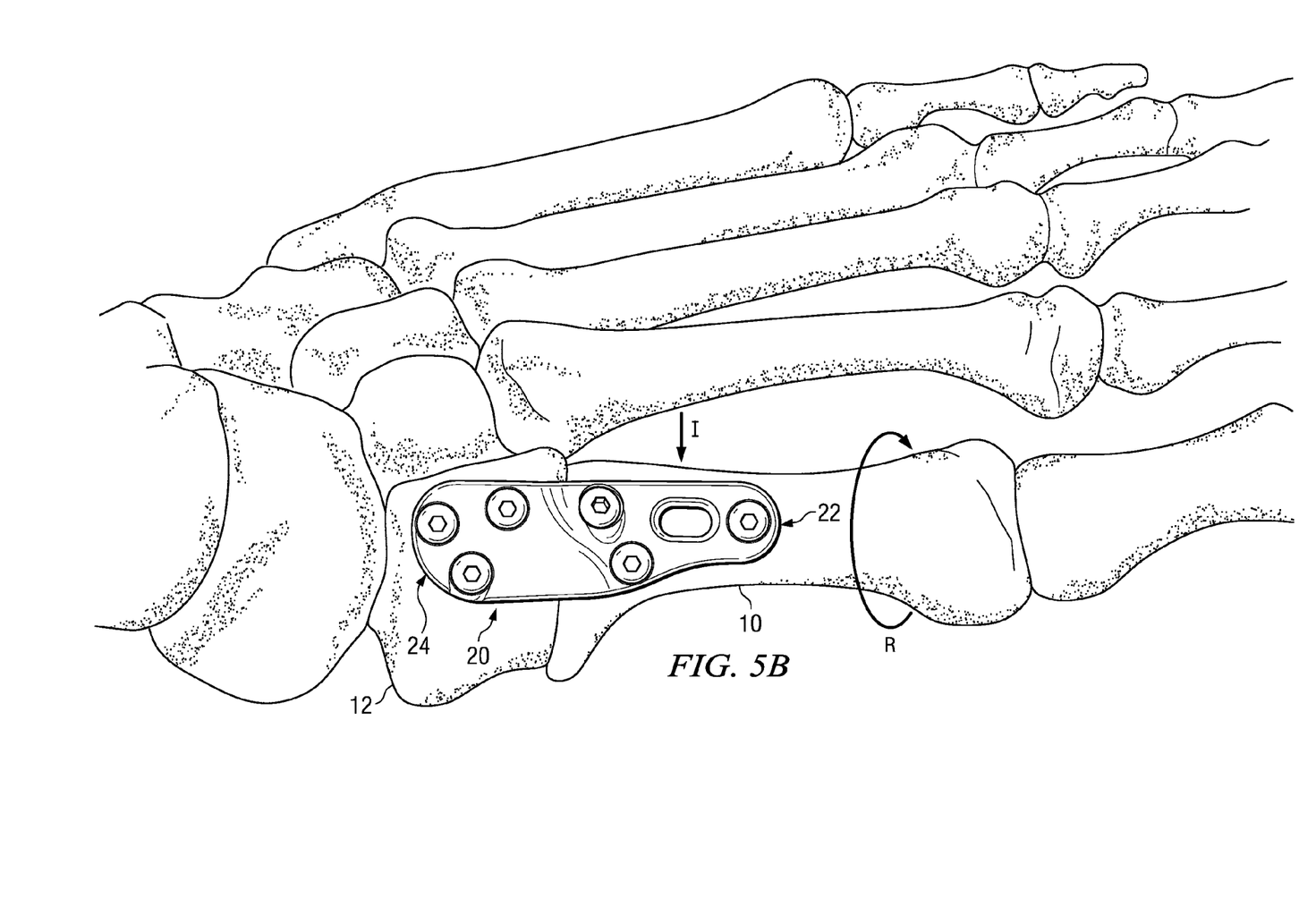
FIG. 5B illustrates another perspective view of the fixation plate of FIG. 2 positioned against the medial cuneiform and first metatarsal.
Figure 6:
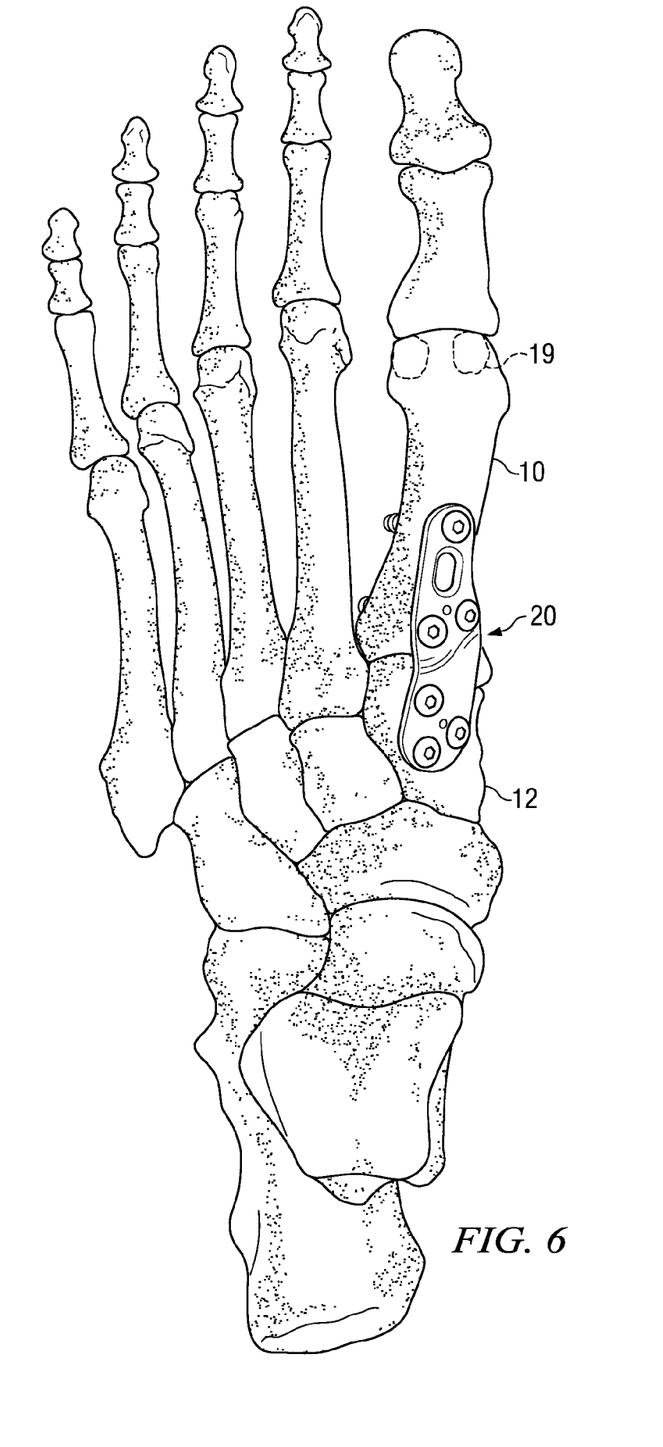
FIG. 6 illustrates a top view of the fixation plate of FIG. 2 affixed to the medial cuneiform and first metatarsal.

In practice, the first MCJ is prepared for plate implantation by first performing a capsulotomy of the ligaments surrounding the first MCJ and then removing cartilage within this joint. Referring to FIGS. 5A, 5B and 6, the proximal portion 24 of the plate 20 is placed against the medial cuneiform 12 and attached thereto using screws 70 having threaded heads and threaded shafts. The threaded heads of the screws 70 thread into the corresponding countersunk threaded holes 48, 50 and 52 (FIG. 2) such that the screws are fixed relative to the plate 20. It is to be appreciated that in some embodiments, the screws may have non-threaded heads such that the screws are not locked into place relative to the plate 20. Upon attachment of the plate 20 to the medial cuneiform 12, the first metatarsal 10 is translated inferiorly in the direction I as illustrated in FIG. 5B to maintain a natural distribution of ground force over all the foot's sesamoid bones to avoid stress fracture or even breakage of the other four metatarsals. In some embodiments, the optimal amount of translation $D_I$ is 3+/−3 mm to accommodate for the shortening that occurs when cartilage is removed from the joint. The first metatarsal 10 is also translated laterally and rotated in the direction R to return the metatarsal to its approximate natural anatomic orientation to reduce the intermetatarsal angle. The plate 20 according to the present disclosure is designed for placement against the medial cuneiform and first metatarsal in an area devoid of muscular and tendinous attachments.

Upon proper positioning of the first metatarsal 10, a screw (not shown) is placed through the elongated hole 44 and into the metatarsal with the elongation permitting movement of the bone. In some embodiments, the MCJ may be temporarily fixated in a corrected position using a k-wire. Also, the plate 20 may include k-wire holes such that k-wires can be used in conjunction with the plate to stabilize the first metatarsal for screw implantation. Upon stabilization, the first metatarsal 10 is then moved toward the medial cuneiform 12 whereupon the screw positioned through elongated hole 44 is tightened to compress the first MCJ. Once compression is achieved, the distal portion 22 of the plate 20 is further attached to the metatarsal using threaded screws 70 having threaded heads that are placed through screw holes 40, 42 and 46 (FIG. 2) and into the bone. The threaded heads of the screws 70 thread into the corresponding countersunk threaded holes 40, 42 and 46 such that the screws are fixed relative to the plate 20. It is to be appreciated that in some embodiments, the screws may have non-threaded heads such that the screws are not locked into place relative to the plate 20. Once the plate is fixed to the medial cuneiform 12 and the first metatarsal 10, the screw passing through elongated hole 44 may be removed.

Figure 7:
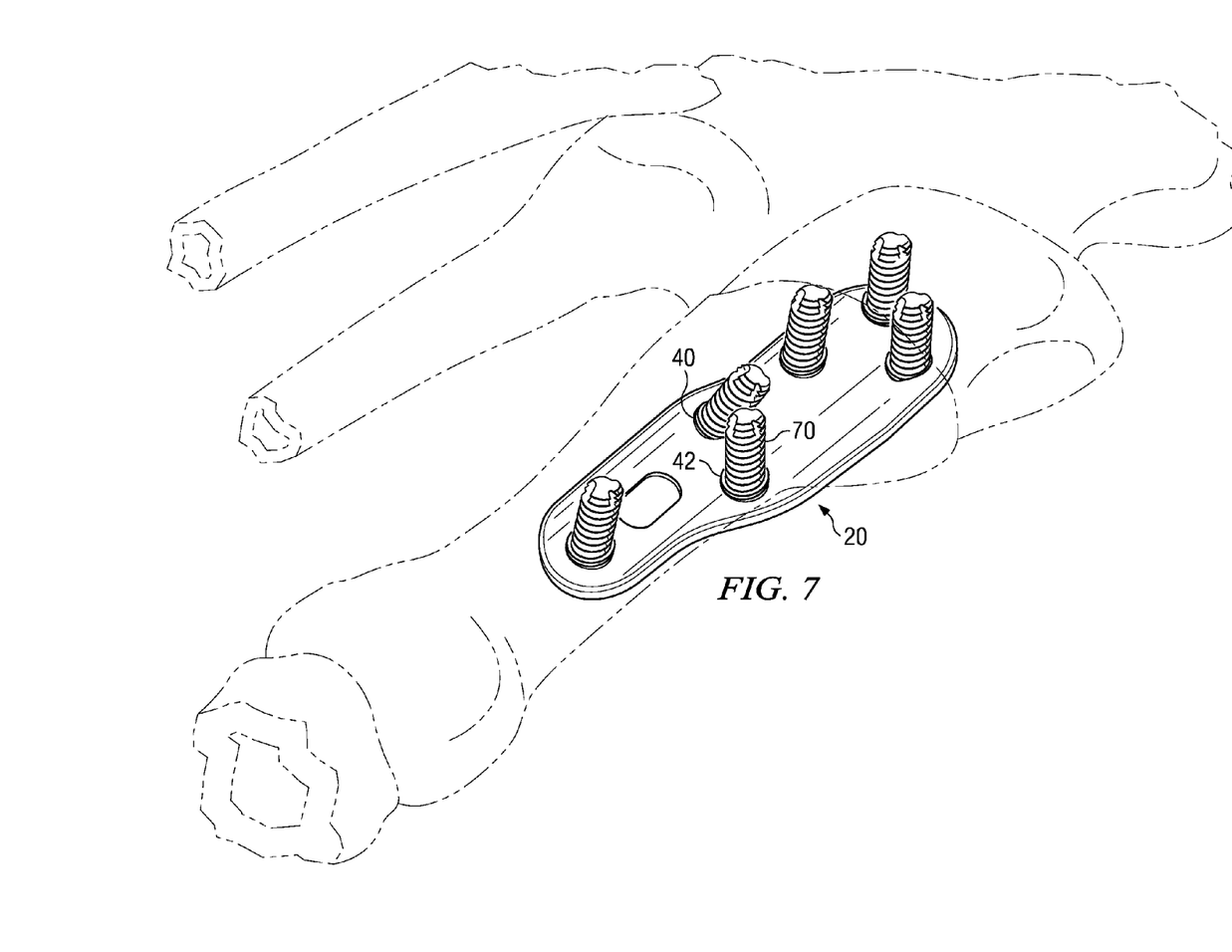
FIG. 7 is a bottom perspective view of the fixation plate of FIG. 6 showing the orientation of the screws.

Referring to FIG. 7, the twist of the plate 20 along its longitudinal axis facilitates desired orientation of the screws into the metatarsal. More specifically, holes 40 and 42 are angled toward one another such that implantation of the screws 70 through these holes results in their axes crossing one another in a divergent manner. This, in turn, provides for optimal orientation of the screws 70 in the first metatarsal 10 to achieve desired stability.

Figure 8:
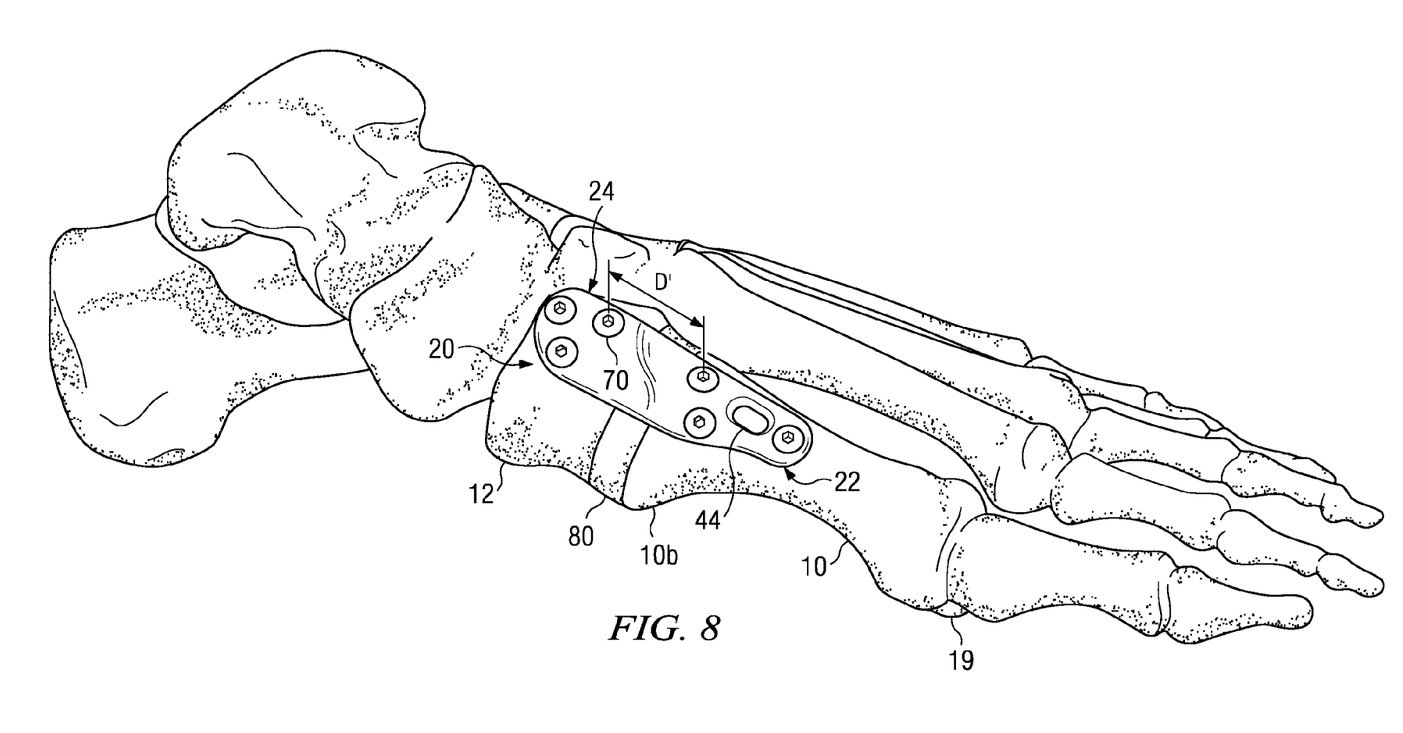
FIG. 8 is a perspective view of another embodiment of the fixation plate wherein the plate is a distraction plate.

A variation of the Lapidus plate according to the present disclosure involves providing for distraction (or lengthening) at the fusion site. As illustrated in FIG. 8, this allows for bone graft 80 to be interposed between the $1^{st}$ metatarsal base 10b and the medial cuneiform 12, when the clinical situation arises. Providing for distraction at the fusion site maintains that the screw holes 40 and 42 purchase the $1^{st}$ metatarsal base 10b, for which these holes are configured to provide maximal stability at the fusion site. The amount of distraction D' most commonly required is between 1 mm-25 mm, with the distraction plate accommodating this length. It is to be appreciated, however, that other distraction lengths may be accommodated by the plate 20 of the present disclosure. In some embodiments, the plate 20 may add length by providing additional screw holes formed in distal portion 22 of the plate 20. In some embodiments, fixation of the plate may occur via a screw passing through the fusion site into the intermediate cuneiform and/or second metatarsal.

The Lapidus plate 20 described herein and associated method of implantation leads to fusion of the MCJ, which provides for mechanical stability of the first metatarsal and medial cuneiform and the reorientation to compensate for an HAV deformity. The orientation of the fixation achieved according to the principles of the present disclosure offers multiplanar stability including the plantar aspects of the MCJ to resist tensile forces across the fusion site. The screw configuration described herein can thus be maintained for several different sizes of distraction Lapidus arthrodesis. That is, the screw configuration provides multiplanar stability as distraction length is added to the plate 20.

While various embodiments of Lapidus plates and related methods of implanting such plates, have been described above, it should be understood that they have been presented by way of example only, and not limitation. Thus, the breadth and scope of the invention(s) should not be limited by any of the above-described exemplary embodiments, but should be defined only in accordance with the following claims and their equivalents. Moreover, the above advantages and features are provided in described embodiments, but shall not limit the application of the claims to processes and structures accomplishing any or all of the above advantages.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field," the claims should not be limited by the language chosen under this heading to describe the so-called technical field. Further, a description of a technology in the "Background" is not to be construed as an admission that technology is prior art to any invention(s) in this disclosure. Neither is the "Brief Summary" to be considered as a characterization of the invention(s) set forth in the claims found herein. Furthermore, any reference in this disclosure to "invention" in the singular should not be used to argue that there is only a single point of novelty claimed in this disclosure. Multiple inventions may be set forth according to the limitations of the multiple claims associated with this disclosure, and the claims accordingly define the invention(s), and their equivalents, that are protected thereby. In all instances, the scope of the claims shall be considered on their own merits in light of the specification, but should not be constrained by the headings set forth herein.

What is claimed is:

1. A device, comprising: a plate adapted for fixation across a metatarsocuneiform joint, the plate including a joint axis defined to lie across the metatarsocuneiform joint, an upper surface and a bone-contacting surface opposite to the upper surface, the plate including a curvature directed towards the bone-contacting surface along a longitudinal axis of the plate, and the plate including a bend about a second axis different from the longitudinal axis and directed toward the bone-contacting surface, a proximal portion adapted for fixation to a cuneiform, the proximal portion including a first hole adjacent to the joint axis and a second hole proximal to the first hole, and a distal portion adapted for fixation to a metatarsal, the distal portion including a third hole adjacent to the joint axis and a fourth hole distal to the third hole, wherein the proximal and distal portions are divided along the joint axis, a first line segment is defined from a center of the first hole to a center of the second hole, a second line segment is defined from the center of the second hole to a center of the third hole, a third line segment is defined from the center of the third hole to a center of the fourth hole, a fourth line segment is defined from the center of the fourth hole to the center of the first hole, the first line segment, second line segment, third line segment and fourth line segment define a substantially trapezoidal arrangement across the joint axis, and wherein a width of the distal portion is 10.5+/−3 millimeters.

2. The device according to claim 1, wherein
the distal and proximal portions include end portions, and the plate increases in width from the distal end portion to the proximal end portion.

3. The device according to claim 2, wherein the width of the proximal end portion is 16+/−4 millimeters.

4. The device according to claim 1, further comprising a recess defined along the bone-contacting surface in a region corresponding to the joint axis of the plate.

5. The device according to claim 4, further comprising a channel formed in the recess to provide flexibility.

6. The device according to claim 1, wherein the plate has a gradual twist along a longitudinal axis defined from the proximal portion to the distal portion.

7. The device according to claim 6, wherein the plate twists approximately 12+/−6 degrees along the longitudinal axis.

8. The device according to claim 1, wherein the holes are countersunk and threaded.

9. The device according to claim 1, further comprising another hole defined proximal of the first and second holes, the another hole being countersunk and threaded.

10. The device according to claim 9, further comprising two additional holes defined distal of the third and fourth holes, one of the two additional holes having an elongated configuration and the other of the two additional holes being countersunk and threaded.

11. The device according to claim 10, wherein the three countersunk holes in the proximal portion are oriented in a triangular arrangement and wherein the three countersunk holes in the distal portion are oriented in a triangular arrangement.

12. The device according to claim 1, wherein the plate accommodates a distraction length of 1 millimeter to 25 millimeters.

13. The device according to claim 1, wherein
the substantially trapezoidal arrangement defines substantially parallel sides and non-parallel sides,
the substantially non-parallel sides of the substantially trapezoidal arrangement define an angle θ between 42 degrees and 72 degrees, and
a distance D between the first hole of the proximal portion and the third hole of the distal portion is between 8 millimeters and 16 millimeters.

14. A method for fusing a metatarsocuneiform joint, comprising:
positioning a fixation plate adjacent to a medial cuneiform, the plate adapted for fixation across a metatarsocuneiform joint, the plate including a joint axis defined to lie across the metatarsocuneiform joint, an upper surface and a bone-contacting surface opposite to the upper surface, the plate including a curvature directed towards the bone-contacting surface along a longitudinal axis of the plate, and the plate including a bend about a second axis different from the longitudinal axis and directed toward the bone-contacting surface,
a proximal portion adapted for fixation to a cuneiform, the proximal portion including a first hole adjacent to the joint axis and a second hole proximal to the first hole, and
a distal portion adapted for fixation to a metatarsal, the distal portion including a third hole adjacent to the joint axis and a fourth hole distal to the third hole, wherein the proximal and distal portions are divided along the joint axis, a first line segment is defined from a center of the first hole to a center of the second hole, a second line segment is defined from the center of the second hole to a center of the third hole, a third line segment is defined from the center of the third hole to a center of the fourth hole, a fourth line segment is defined from the center of the fourth hole to the center of the first hole,
the first line segment, second line segment, third line segment and fourth line segment define a substantially trapezoidal arrangement across the joint axis, and wherein a width of the distal portion is 10.5+/−3 millimeters,
securing the plate to the cuneiform using three screws triangularly oriented through the plate;
laterally and inferiorly translating and rotating a metatarsal such that an end of the metatarsal abuts the cuneiform and fits into the recess defined by the plate; and securing the plate to the metatarsal using three screws triangularly oriented through the plate.

15. A method according to claim 14, wherein the metatarsal is inferiorly translated a distance of 3+/−3 mm.

16. A method according to claim 14, further comprising the step of compressing the metatarsocuneiform joint before securing the plate to the metatarsal.

17. A method according to claim 14, wherein the plate has a gradual twist from the proximal portion to the distal portion to match the contour of the metatarsal after rotation of the metatarsal.

18. A method according to claim 14, further comprising the step of securing the plate to a second metatarsal.

19. A method according to claim 14, further comprising the step of securing the plate to an intermediate cuneiform.

20. A method according to claim 14, wherein the fixation plate is designed for placement against an area of the medial cuneiform and first metatarsal that is devoid of muscular or tendinous attachments.

* * * * *